United States Patent [19]

Meserve

[11] Plant 4,804

[45] Jan. 19, 1982

[54] ILEX PLANT—MESAN VARIETY

[75] Inventor: Kathleen K. Meserve, St. James, N.Y.

[73] Assignee: Conard-Pyle Company, West Grove, Pa.

[21] Appl. No.: 163,273

[22] Filed: Jun. 26, 1980

[51] Int. Cl.[3] ..... A01H 5/00

[52] U.S. Cl. ..... Plt./65

[58] Field of Search ..... Plt./65

*Primary Examiner*—James R. Feyrer

*Attorney, Agent, or Firm*—Burns, Doane, Swecker & Mathis

[57] ABSTRACT

A new and distinct variety of *Ilex*×*meserveae* which originated as a cross-pollination of *Ilex aquifolium* and *Ilex rugosa* is provided. The new variety possesses very attractive, glossy, deep green foliage, produces an abundance of staminate flowers, and exhibits a vigorous growth characteristic and good tolerance to cold.

2 Drawing Figures

SUMMARY OF THE INVENTION

My invention relates to a new, distinctive and useful form of *Ilex*×*meserveae* originated by me by crossing an unnamed and unpatented seedling of the species known botanically as *Ilex aquifolium* with an unnamed and unpatented seedling of the species known botanically as *Ilex rugosa.*

The object of my breeding was to create a hardy, vigorous and versatile shrub of attractive appearance which combined the beauty of the *Ilex aquifolium* foliage with the hardiness of *Ilex rugosa.* This objective was successfully achieved, and the new variety exhibits a combination of characteristics which distinguish it from all offspring resulting from the same cross, as well as all other forms of Ilex of which I am aware.

The following combination of characteristics is exhibited by the new variety:

(a) a well branched and upright habit of growth which is more vigorous than that of Blue Prince variety (U.S. Plant Pat. No. 3,517) and which is much more vigorous and more upright than Blue Boy variety (U.S. Plant Pat. No. 2,435), (b) a more compact and shrub-like habit of growth than *Ilex aquifolium,*

(c) an abundance of staminate flowers which appear in spring, and, in lesser quantities, throughout the entire growing season and which produce the pollen necessary for fertilizing the pistilate flowers of other varieties of *Ilex*×*meserveae* and other forms of Ilex, (d) the ability to be sheared and trimmed to be kept within prescribed limits or shaped to a particular shape or form, (e) cold tolerance which is superior to its *aquifolium* parent, (f) deep, slightly glaucous, green foliage which is longer and wider than that of Blue Prince variety and considerably longer and wider than that of Blue Boy variety, (g) less prominent spines than Blue Prince variety or Blue Boy variety, which, combined with the vigorous upright habit of growth, make the present variety especially well suited for use as snag-free hedging by walkways and other places where there is considerable traffic, and, (h) growth characteristics which make it superior in field production from a cultural standpoint to other male *Ilex*×*meserveae.*

Approximately seventy percent of two year old container grown plants of the present variety measure approximately 15 to 18 inches in height and breadth when grown at West Grove, Pa. For comparative purposes approximately fifty-five percent of two year old plants of the Blue Prince variety measure approximately 15 to 18 inches in height and breadth under the same growing conditions, and in excess of fifty percent of two year old plants of the Blue Boy variety measure approximately 12 to 15 inches in height and breadth under the same growing conditions. The size disparity between the present variety and the Blue Prince and Blue Boy varieties is more pronounced when the plants are grown in the field or landscape.

The present variety has successfully withstood in the absence of defoliation or other damage winter temperatures of approximately −15° F. when field grown.

Asexual reproduction, by cuttings, of my new plant has been accomplished at St. James, N.Y., and at West Grove, Pa. Succeeding propagations have shown the unique combination of characteristics is fully established and transmitted to successive generations.

The new variety has been named the Mesan variety.

BRIEF DESCRIPTION OF THE PHOTOGRAPHS

The accompanying photographs show typical specimens of my new variety of Ilex during late May as depicted in color as true as is reasonably possible to make the same in color photographs of this character. The specimens in the photographs were grown in the ground at West Grove, Pa.

FIG. 1 shows a typical four year old plant of the present variety.

FIG. 2 shows typical branches and leaves of the present variety. The current year's growth and the prior year's growth are apparent on the branches. The upper and lower surfaces of the leaves are shown.

DETAILED DESCRIPTION

Figure 1:
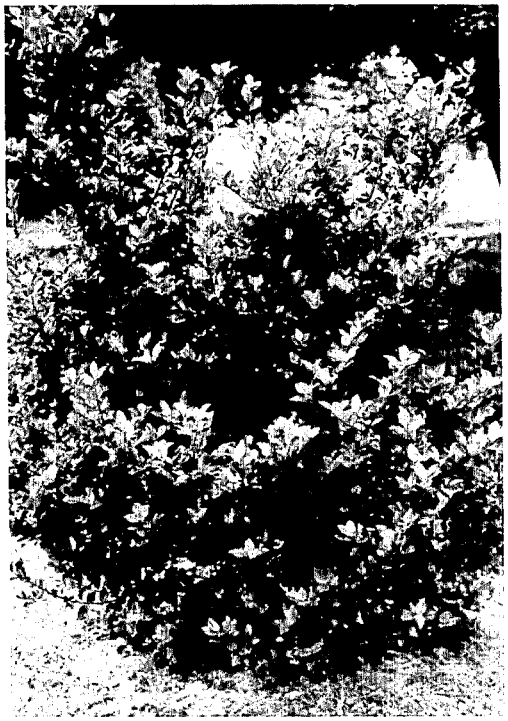
Figure 2:
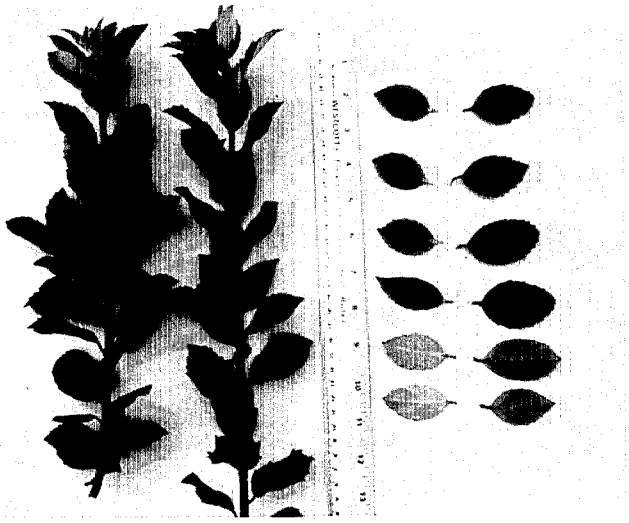

The following is a detailed description of my new variety made from four year old plants growing in the ground at West Grove, Pa. Color terminology is made in accordance with The R. H. S. Colour Chart of The Royal Horticultural Society, London, England.

Class: *Ilex*×*meserveae*

Parentage: *Ilex aquifolium* seedling×*Ilex rugosa* seedling

Foliage:

*Type.*—Evergreen. Leaves mostly eliptic in shape, with a few leaves ovate. Apex acute, base obtuse. Margins serrate with from ten to fifteen spines. Spines are much less pronounced than on Blue Boy and Blue Prince.

*Size.*—Mature leaves on main stem (measurements to tips of spines) — length from approximately 3.9 to 6.6 cm., with an average of approximately 5.9 cm.; width from approximately 2.5 to 4.0 cm., with an average of approximately 3.5 cm.

*Color.*—Mature leaves in late May, upper side — Green Group 139A; under side — Green Group 143A. Mature leaves are quite glossy, although less glossy than Blue Prince. Immature leaves, upper side — Green Group 141A; under side — Yellow-Green Group 144A–144B.

Stems:

*Color.*—In late May, Purple Group 79B.

Flowers: Flowers are not substantially different from staminate flowers of the instant species.

I claim:

1. A new and distinct variety of *Ilex×meserveae,* substantially as herein shown and described, characterized particularly as to novelty by the unique combination of:

(a) a well branched and upright habit of growth which is more vigorous than that of Blue Prince variety (U.S. Plant Pat. No. 3,517) and which is much more vigorous and more upright than Blue Boy variety (U.S. Plant Pat. No. 2,435), (b) a more compact and shrub-like habit of growth than *Ilex aquifolium,*

(c) an abundance of staminate flowers which appear in spring, and, in lesser quantities, throughout the entire growing season and which produce the pollen necessary for fertilizing the pistilate flowers of other varieties of *Ilex×meserveae* and other forms of Ilex, (d) the ability to be sheared and trimmed to be kept within prescribed limits or shaped to a particular shape or form, (e) cold tolerance which is superior to its *aquifolium* parent, (f) deep, slightly glaucous, green foliage which is longer and wider than that of Blue Prince variety and considerably longer and wider than that of Blue Boy variety, (g) less prominent spines than Blue Prince variety or Blue Boy variety, which, combined with the vigorous upright habit of growth, make the present variety especially well suited for use as snag-free hedging by walkways and other places where there is considerable traffic, and, (h) growth characteristics which make it superior in field production from a cultural standpoint to other male *Ilex×meserveae.*

* * * * *